United States Patent
Siurkus et al.

(10) Patent No.: US 11,268,084 B2
(45) Date of Patent: Mar. 8, 2022

(54) GLYCEROL-FREE FORMULATIONS FOR REVERSE TRANSCRIPTASES

(71) Applicant: THERMO FISHER SCIENTIFIC BALTICS UAB, Carlsbad, CA (US)

(72) Inventors: Juozas Siurkus, Vilnius (LT); Darius Kavaliauskas, Vilnius (LT); Daumantas Matulis, Vilnius (LT); Lina Baranauskiene, Vilnius (LT)

(73) Assignee: Thermo Fisher Scientific Baltics, UAB, Vilnius (LT)

( * ) Notice: Subject to any disclaimer, the term of this patent is extended or adjusted under 35 U.S.C. 154(b) by 0 days.

(21) Appl. No.: 16/635,934

(22) PCT Filed: Aug. 2, 2018

(86) PCT No.: PCT/EP2018/071037
§ 371 (c)(1),
(2) Date: Jan. 31, 2020

(87) PCT Pub. No.: WO2019/030118
PCT Pub. Date: Feb. 14, 2019

(65) Prior Publication Data
US 2020/0248167 A1    Aug. 6, 2020

Related U.S. Application Data

(60) Provisional application No. 62/542,710, filed on Aug. 8, 2017.

(51) Int. Cl.
*C12N 9/96*    (2006.01)
*C12N 9/12*    (2006.01)
*C12N 15/10*   (2006.01)

(52) U.S. Cl.
CPC ............ *C12N 9/96* (2013.01); *C12N 9/1276* (2013.01); *C12N 15/1096* (2013.01); *C12Y 207/07049* (2013.01)

(58) Field of Classification Search
None
See application file for complete search history.

(56) References Cited

U.S. PATENT DOCUMENTS

| | | |
|---|---|---|
| 5,834,254 A | 11/1998 | Shen et al. |
| 2008/0227661 A1* | 9/2008 | Hogrefe ............... C40B 50/06 506/26 |
| 2011/0014676 A1 | 1/2011 | Cowan et al. |
| 2014/0199749 A1 | 7/2014 | Lee et al. |

FOREIGN PATENT DOCUMENTS

| | | |
|---|---|---|
| EP | 0791650 A1 | 8/1997 |
| WO | WO-1999067371 A1 | 12/1999 |
| WO | WO-2016033116 A1 | 3/2016 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Carninci P et al., "Thermostabilization and thermoactivation of thermolabile enzymes by trehalose and its application for the synthesis of full length cDNA," Proceedings of the National Academy of Sciences, USA, vol. 95, No. 2, Jan. 1998, pp. 520-524.
Fagain C.O et al., "Understanding and increasing protein stability", Biochimica et Biophysica Acta, vol. 1252, No. 1, Sep. 27, 1995, pp. 1-14.
Gerard et al., "Reverse Transcriptase. The Use of Cloned Moloney Murine Leukemia Virus Reverse Transcriptase to Synthesize DNA from RNA", Molecular Biotechnology, vol. 8, No. 1, Aug. 1997, pp. 61-77.
Hamada et al., "Effect of additives on protein aggregation", Current Pharmaceutical Biotechnology, vol. 10, No. 4, Jun. 2009, pp. 400-407.
Iyer et al., "Enzyme Stability and Stabilization-Aqueous and Non-Aqueous Environment," Process Biochemistry, Elsevier LTD, GB, vol. 43, No. 10, Oct. 1, 2008 (Oct. 1, 2008), pp. 1019-1032.
Jaenicke R: "Stability and stabilization of globular proteins in solution", Journal of Biotechnology, vol. 79, No. 3, May 2000, pp. 193-203.
Konishi et al., "Stabilization of Moloney murine leukemia virus reverse transcriptase by site-directed mutagenesis of surface residue Val433", Bioscience Biotechnology and Biochemistry, vol. 78, No. 1, Apr. 2014, pp. 75-78.
Mizuno et al., "Insight into the mechanism of the stabilization of moloney murine leukaemia virus reverse transcriptase by eliminating RNase H activity", Biosci Biotechnol Biochem, vol. 74, No. 2, 2010, pp. 440-442.
PCT/EP2018/071037, Search Report and Written Opinion, dated Oct. 23, 2018, pp. 1-10.
Vagenende et al., "Mechanisms of protein stabilization and prevention of protein aggregation by glycerol", Biochemistry, vol. 48, No. 46, Nov. 2009, pp. 11084-11096.

* cited by examiner

*Primary Examiner* — Christian L Fronda
(74) *Attorney, Agent, or Firm* — Priya D. Subramony

(57) ABSTRACT

Glycerol-free enzyme formulations are described. In some embodiments, a glycerol-free enzyme formulation is stabilized by high salt concentration. The glycerol free enzyme formulation may comprise a reverse transcriptase enzyme.

9 Claims, 4 Drawing Sheets

Specification includes a Sequence Listing.

GLYCEROL-FREE FORMULATIONS FOR REVERSE TRANSCRIPTASES

CROSS REFERENCE TO RELATED APPLICATION

This application is a 371 U.S. National Phase Application of PCT/EP2018/071037 filed Aug. 2, 2018, which claims priority to and the benefit of U.S. Provisional Patent Application No. 62/542,710 filed Aug. 8, 2017, which applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 25, 2018, is named LT01278PCT_SL.txt and is 12,663 bytes in size.

FIELD

Stabilizing effect and storage buffer composition for reverse transcription enzymes used for nucleic acid amplification.

BACKGROUND

The synthesis of single-stranded complementary DNA (cDNA) from RNA is called reverse transcription and the enzyme catalyzing the reaction is called RNA-directed DNA polymerase (reverse transcriptase). The first retroviral enzyme used to prepare cDNA was purified from avian myeloblastosis virus (AMV). Later, Moloney murine leukemia virus (MMLV) reverse transcriptase was cloned, overexpressed and purified from *Escherichia coli*. Reverse transcriptases synthesize cDNA in the presence of a preformed primer to the template polyribonucleotide, a divalent metal ion and a mixture of four deoxyribonucleoside triphosphates (dNTPs). (Gerard G F et al., Reverse transcriptase: The use of cloned Moloney murine leukemia virus reverse trancriptase to synthesize DNA from RNA, *Mol Biotechnol.* 8(1):61-77 (1997). In general reverse transcription enzymes tend to show low processivity, they have a tendency to pause at secondary structure RNA elements, they do not possess endogenous 3→5' exonuclease activity, show template switching activity (Luo G X et al, Template switching by reverse transcriptase during DNA synthesis, *J Virol.* 64(9): 4321-8 (1990)) and strand displacement properties (Whiting S H et al, Properties of strand displacement synthesis by moloney murine leukemia virus reverse transcriptase: mechanistic implications, *J Mol Biol.* 278(3):559-77 (1998)). Reverse transcriptases contain RNase H domain which is necessary to digest parental RNA molecule to liberate the cDNA from the RNA-DNA hybrid after reverse transcription. During in vitro DNA synthesis, it was observed that removal of RNase H activity increased the efficiency of reverse transcription and thermal stability of MMLV reverse transcriptase (Mizuno M et al, Insight into the mechanism of the stabilization of Moloney murine leukemia virus reverse transcriptase by eliminating RNase H activity, *Biosci Biotechnol Biochem.* 74(2):440-2 (2010). Thermal stabilization effect was also observed when reverse transcriptase was bound to template-primer complex (Gerard G F et al, The role of template-primer in protection of reverse transcriptase from thermal inactivation, *Nucleic Acids Res.* 30(14):3118-29 (2002). To avoid RNA secondary structures and primer nonspecific binding to the template during in vitro cDNA synthesis, MMLV RT enzyme was extensively mutagenized resulting in many different mutations which increased enzyme's thermal stability at elevated reaction temperatures (Konishi A et al, Stabilization of Moloney murine leukemia virus reverse transcriptase by site-directed mutagenesis of surface residue Va1433, *Biosci Biotechnol Biochem.* 78(1):75-8 (2014).

Proteins have a particular structural organization and conformational flexibility in solution. In order to stabilize them, various additives are usually supplemented to protect their structure and function. Typically, inclusion of low molecular weight compounds up to 1M increase protein stability in solution. These additives can be ionic stabilizers or osmolytes that are uncharged and that affect solvent viscosity and surface tension. These osmolytes include polyols, sugars and amino acids (Jaenicke R. Stability and stabilization of globular proteins in solution. 2000. *J. Biotechnol.* 79(3):193-203). Organic salts like ethylammonium nitrate are known to act as a refolding additive. Certain amino acids like proline, histidine, arginine were reported to be protein aggregation suppressors. Arginine has been used for refolding and/or stabilization of number of aggregation-prone, disulfide bonds comprising recombinant proteins (see US20110014676A1). Polyamines are usually used up to 0.1M concentration to reduce heat-induced protein aggregation. Amphiphilic polymers like polyethylene glycol or polyvinylpyrrolidone stabilize the hydrophobic surface of aggregation-prone intermediates and increase the rate of refolding (Hamada H, Arakawa T, Shiraki K. Effect of additives on protein aggregation. 2009. *Curr Parm Biotechnol.* 10(4):400-7).

Glycerol is another additive that plays a role in preferential hydration of proteins and produces an electrostatic interaction with protein surface to induce more compact protein conformations. Glycerol reduces protein flexibility and also stabilizes partially unfolded protein intermediates. Glycerol prevents protein aggregation by interacting with hydrophobic regions of protein structure to favor amphiphilic interface orientations of glycerol [Vagenende V, Yap M G, Trout B L. 2009. Mechanisms of protein stabilization and prevention of protein aggregation by glycerol. *Biochemistry.* 48(46):11084-96].

Another important additive which is known to stabilize dilute protein solutions is bovine serum albumin (BSA). BSA is thought to protect proteins by stabilizing their native conformation and protecting against adsorption effect to surfaces. BSA was also shown to bind to interact with proteins through hydrophobic areas on their surface leading to thermostabilization (Chang B S, Mahoney R R. 1995. Enzyme thermostabilization by bovine serum albumin and other proteins: evidence for hydrophobic interactions. *Biotechnol Appl Biochem.* 22 (Pt 2):203-14). Protein refolding can be attained by reforming the incorrect disulfide bridges within the structure of the protein. Oxidized and reduced forms of glutathione are normally used (GSSG, GSH) (Cabrita L D, Bottomley S P. 2004. Protein expression and refolding—a practical guide to getting the most out of inclusion bodies. *Biotechnol Annu Rev.* 10:31-50).

Sometimes proteins are stabilized by chemically modifying specific amino acids located at the surface of the protein. The most common approaches used rely on inter- and intramolecular chemical cross-linking of proteins by using bifunctional reagents, surface group modification and covalent coupling of polymers like polyethylene glycol or polysaccharides (Fagain C O. Understanding and increasing protein stability. 1995. *Biochim Biophys Acta.* 1252(1):1-14).

In general, reverse transcriptases are not very stable enzymes. Moloney murine leukemia virus (MMLV) reverse transcriptase aggregates easily, and it is thought that formation of intermolecular disulfide bonds and intermolecular interaction of hydrophobic surfaces are the main reasons of aggregation (Konishi A, Ma X, Yasukawa K. Stabilization of Moloney murine leukemia virus reverse transcriptase by site-directed mutagenesis of surface residue Val433. 2014. *Biosci Biotechnol Biochem.* 78(1):75-8). To reduce MMLV reverse transcriptase denaturation, a reducing agent like DTT is typically included in the storage solution and 50% glycerol is used in all formulations. It is also recommended to include 0.1M of NaCl and a detergent in reverse transcriptase storage buffers (Gerard G F, Fox D K, Nathan M, D'Alessio J M. 1997. Reverse transcriptase. The use of cloned Moloney murine leukemia virus reverse trancriptase to synthesize DNA from RNA. *Mol Biotechnol.* 8(1):61-77). Inclusion of sugars like trehalose into the reaction buffer has also resulted in thermoactivation and thermostabilization of MMLV reverse transcriptase. Addition of up to 0.6M trehalose into the reverse transcription reaction mixture showed greater activity of MMLV RT at higher reaction temperatures, and the enzyme was able to produce longer cDNA molecules (Carninci P, Nishiyama Y, Westover A, Itoh M, Nagaoka S, Sasaki N, Okazaki Y, Muramatsu M, Hayashizaki Y. Thermostabilization and thermoactivation of thermolabile enzymes by trehalose and its application for the synthesis of full length cDNA. 1998. *Proc Natl Acad Sci USA.* 95(2):520-4).

Reverse transcriptase can also be successfully stabilized and lyophilized in a glycerol-free environment. Inclusion of sugars like sucrose or trehalose, addition of polymer polivinylpyrrolidone, and a reducing agent N-acetyl-L-cysteine protected the structure and activity of MMLV reverse transcriptase and resulted in the intact protein after a freeze-drying process [See U.S. Pat. No. 5,834,254]. Polymers such as e.g. polyvinylpyrrolidone may form overly compact and hard lyophilized composition that can be difficult to dissolve.

Other polyols can be also used as cryoprotectants, for example, sorbitol or xylitol.

High-salt glycerol-free formulations are described herein that protect MMLV reverse transcriptase enzymatic activity and allow lyophilization. Additional stabilization may be achieved using a sugar stabilizer in the formulation.

SUMMARY

The growing field of medical diagnostics demands reverse transcription enzymes (RT) in various formats including master mixes in glycerol-free formulations. However, without glycerol the RT enzymes are highly unstable, thus a main technical challenge is to develop compositions to ensure stability of RT enzymes in a glycerol-free environment for long-term storage, transportation and/or direct application to freeze-drying process. Therefore, non-glycerol based stabilizing compounds for stabilization of MMLV H-reverse transcriptases were assessed with the aim to derive a lyophilization-compatible composition, which would be stable at the various storage conditions.

The presence of glycerol in the enzyme buffer makes freeze-drying or drying complicated. Since glycerol is hygroscopic, its presence in the final freeze-dried product likely results in a high moisture content, which may affect the stability of the product. Glycerol also interferes with applications where viscosity of the liquid is important, such as automated dispensing or high throughput testing (e.g. in higher density plate formats such as 384- and 1,536-well plates). Pipetting of such viscous solutions can prevent accurate and reproducible dispensing especially in the nano-liter and microliter volume range. Automated liquid handling machines need to be additionally adjusted in order to dispense viscous liquids that contain high percentage of glycerol.

Glycerol may also not be desirable in the formulations of enzymes that are used for emerging technologies of single cell mRNA sequencing. Glycerol may interfere with surface tension; thus, it may negatively impact formation of droplets, cell lysis, and efficiency of cDNA synthesis.

Described herein is a stabilized enzyme formulation comprising an enzyme and a glycerol-free buffer having high ionic strength comprising salt(s) providing Na+ and/or K+ ions, wherein the high ionic strength is at least 0.5 M ionic strength and further wherein the stabilized enzyme formulation retains at least 70% activity after storage for at least 5 days at 25° C. and/or at least 4 months at −20° C.

In some embodiments, salt(s) further provide Cl; and/or $SO_4^{-2}$ ions.

In some embodiments, the high ionic strength is from 0.5 M to 1.5 M ionic strength. In some embodiments, the high ionic strength is from 0.5 M to 1.0 M ionic strength. In some embodiments, the high ionic strength is from 1.0 M to 1.5 M ionic strength.

In some embodiments, the high ionic strength buffer comprises NaCl. In some embodiments, the concentration of NaCl is from 500 mM to 1500 mM.

In some embodiments, the high ionic strength buffer comprises KCl. In some embodiments, the concentration of KCl is from 500 mM to 1500 mM.

In some embodiments, the high ionic strength buffer comprises $Na_2SO_4$. In some embodiments, the concentration of $Na_2SO_4$ is from 300 mM to 500 mM.

In some embodiments, the high ionic strength buffer comprises $K_2SO_4$. In some embodiments, the concentration of $K_2SO_4$ is from 300 mM to 500 mM.

In some embodiments, the formulation further further comprises at least one of a buffer salt; reducing agent(s); detergent(s); cryoprotectant(s); and/or optional other stabilizer(s).

In some embodiments, the enzyme is a reverse transcriptase. In some embodiments, the reverse transcriptase is an MMLV reverse transcriptase. In some embodiments, the reverse transcriptase is wildtype MMLV reverse transcriptase. In some embodiments, the reverse transcriptase is mutant MMLV reverse transcriptase. In some embodiments, the mutant MMLV reverse transcriptase is RevertAid, Maxima, and/or Superscript III. In some embodiments, the reverse transcriptase is an RNase H+ reverse transcriptase. In some embodiments, the reverse transcriptase is an RNase H− reverse transcriptase. In some embodiments, the reverse transcriptase is Superscript IV RT, AffinityScript Reverse Transcriptase, NxtScript Reverse Transcriptase, RnaUsScript Reverse Transcriptase, SensiScript RT, RocketScript Reverse Transcriptase, GoScript Reverse Transcriptase, and/or Thermoscript reverse transcriptase.

In some embodiments, the melting temperature of the enzyme increases as compared to the same enzyme in a buffer of 50 mM Hepes pH 7.0, 6.7 mM NaCl, 0.1 mM DTT, 0.27% sucrose, and 0.007 mM EDTA. In some embodiments, the melting temperature increases by 0.5° C. to 5° C.

Also disclosed herein is a stabilized enzyme formulation comprising an enzyme and a glycerol-free buffer having high ionic strength comprising salt(s) providing Na+ and/or K+ ions, wherein the high ionic strength is at least 0.3 M ionic strength and further wherein the melting temperature of the enzyme increases as compared to the same enzyme in a buffer of 50 mM Hepes pH 7.0, 6.7 mM NaCl, 0.1 mM DTT, 0.27% sucrose, and 0.007 mM EDTA. In some embodiments, the high ionic strength is at least 0.5 M ionic strength. In some embodiments, the melting temperature increases by 0.5 to 5° C.

In some embodiments, the formulation further comprises sorbitol. In some embodiments, the formulation comprises 20% sorbitol.

In some embodiments, the stability of the formulation is maintained after at least 20 freeze-thaw cycles.

In some embodiments, the concentration of enzyme in the formulation is from 180 to 220 units/μL.

In some embodiments, the formulation is stable for at least 5 days at 25° C.

In some embodiments, the formulation is stable for at least 4 months at −20° C.

In some embodiments, the buffer salt(s) comprise Tris-HCl, HEPES, Bis-Tris, Mes, and/or Mops. In some embodiments, the buffer salt(s) are present at a concentration of from 10-100 mM.

In some embodiments, the formulation has a pH from 6 to 8. In some embodiments, the formulation has a pH of 7.0.

In some embodiments, the reducing agent(s) comprise mercaptoethanol, DTT, TCEP, NALC, and/or GSH/GSSG. In some embodiments, the reducing agent(s) are present at a concentration of from 1-20 mM.

In some embodiments, the detergent(s) comprise non-ionic detergents. In some embodiments, the detergent(s) comprise Triton X-100, Nonidet P-40, Tween 20, Tween 80, Brij 35, Brij 68, Tween 85, Synperonic® detergent, Hecameg® detergent, and/or Elugent™ detergent. In some embodiments, the detergent(s) are present at a concentration of from 0.1% to 1%.

In some embodiments, the cryoprotectant(s) comprise sorbitol, mannose, arabinose, sucrose, rhamnose, mannitol, trehalose, xylose, maltose, raffinose, and/or inulin. In some embodiments, the cryoprotectant(s) are present at a concentration of from 1%-25%.

In some embodiments, the formulation comprises other stabilizer(s). In some embodiments, the other stabilizer(s) comprise arginine, $MgCl_2$, $MgSO_4$, TMAO, PVP, glycine, cysteine, PVA, PEG4000, PEG8000, and/or Ficoll. In some embodiments, the other stabilizer(s) are present at a concentration of from 0.1 to 1 M for arginine; 1-10 mM for $MgCl_2$; 1-10 mM for $MgSO_4$, 0.1 to 1 M for TMAO; 0.1-2% for PVP (polyvinyl-pyrrolidone); 0.1-1 M for glycine; 0.1 to 1 M for cysteine; 0.1 to 2% for PVA; 1-10% for PEG4000; 1-10% for PEG8000; and/or 1-10% for Ficoll.

In some embodiments, the glycerol-free buffer comprises no more than 2% glycerol. In some embodiments, the glycerol-free buffer comprises no more than 1% glycerol. In some embodiments, the glycerol-free buffer comprises no more than 0.5% glycerol. In some embodiments, the glycerol-free buffer comprises no more than 0.1% glycerol. In some embodiments, the glycerol-free buffer does not comprise amino acids.

In some embodiments, the glycerol-free buffer does not comprise peptides. In some embodiments, the glycerol-free buffer does not comprise polypeptides other than the enzyme. In some embodiments, the glycerol-free buffer does not comprise poly(amino acid).

In some embodiments, the stabilized enzyme formulation retains at least 80% activity after storage for at least 5 days at 25° C. and/or at least 4 months at −20° C.

In some embodiments, the stabilized enzyme formulation retains at least 90% activity after storage for at least 5 days at 25° C. and/or at least 4 months at −20° C.

Disclosed herein is also a method of stabilizing an enzyme formulation comprising providing the enzyme and glycerol-free buffer and allowing the glycerol-free buffer to stabilize the enzyme.

Also disclosed herein is a method of storing a stabilized enzyme formulation comprising providing the stabilized enzyme formulation and storing the enzyme formulation for at least 5 days at 25° C. and/or at least 4 months at −20° C., wherein the stabilized enzyme formulation retains at least 70% activity after storage.

In some embodiments, the storage is for at least 5 days at 25° C. In some embodiments, the storage is for at least 4 months at −20° C.

Also disclosed herein is a method of producing complementary DNA (cDNA) from an RNA sample comprising obtaining an RNA sample; mixing the sample with one or more primer, deoxynucleotide triphosphates (dNTPs), and a stabilized enzyme formulation; and incubating the mixture in reaction buffer.

In some embodiments, the cDNA produced is used for a one-step RT-PCR reaction.

In some embodiments, the cDNA produced is used in a separate PCR reaction.

In some embodiments, a stabilized enzyme formulation is diluted with water or buffer before mixing with the RNA sample.

In some embodiments, the cDNA is stored at −20° C. or lower for later use.

In some embodiments, the one or more primer is non-specific. In some embodiments, the non-specific primer is an oligo(dT)$_{18-20}$ (SEQ ID NO: 3) or a random hexamer primer.

In some embodiments, the one or more primer is gene-specific.

In some embodiments, the RNA is total RNA, poly(A) RNA, or specific RNA.

In some embodiments, the reaction buffer comprises RNase inhibitor.

In some embodiments, the incubating in reaction buffer is at between 50° C.-70° C. In some embodiments, the incubating in reaction buffer is for 10-30 minutes.

In some embodiments, the method is used in a high-throughput screening format.

In some embodiments, the method is used with automated liquid handling devices.

In some embodiments, 200 U of reverse transcriptase enzyme is added to a 20 ul reaction with RNA amounts from 1 pg-1 μg total RNA, 0.1 pg-500 ng mRNA, or 0.01 pg-500 ng specific RNA.

Also disclosed herein is a stabilized enzyme formulation comprising an enzyme and a glycerol-free buffer having high ionic strength comprising salt(s) providing Na+ and/or K+ ions; wherein the high ionic strength is at least 0.3 M ionic strength and further wherein the stabilized enzyme formulation retains at least 70% activity after storage for at least 5 days at 25° C. and/or at least 4 months at −20° C.

In some embodiments, the high ionic strength buffer comprises $Na_2SO_4$ or $K_2SO_4$. In some embodiments, the concentration of $Na_2SO_4$ or $K_2SO_4$ is from 100 mM to 500 mM.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

DESCRIPTION OF THE SEQUENCES

Figure 1:
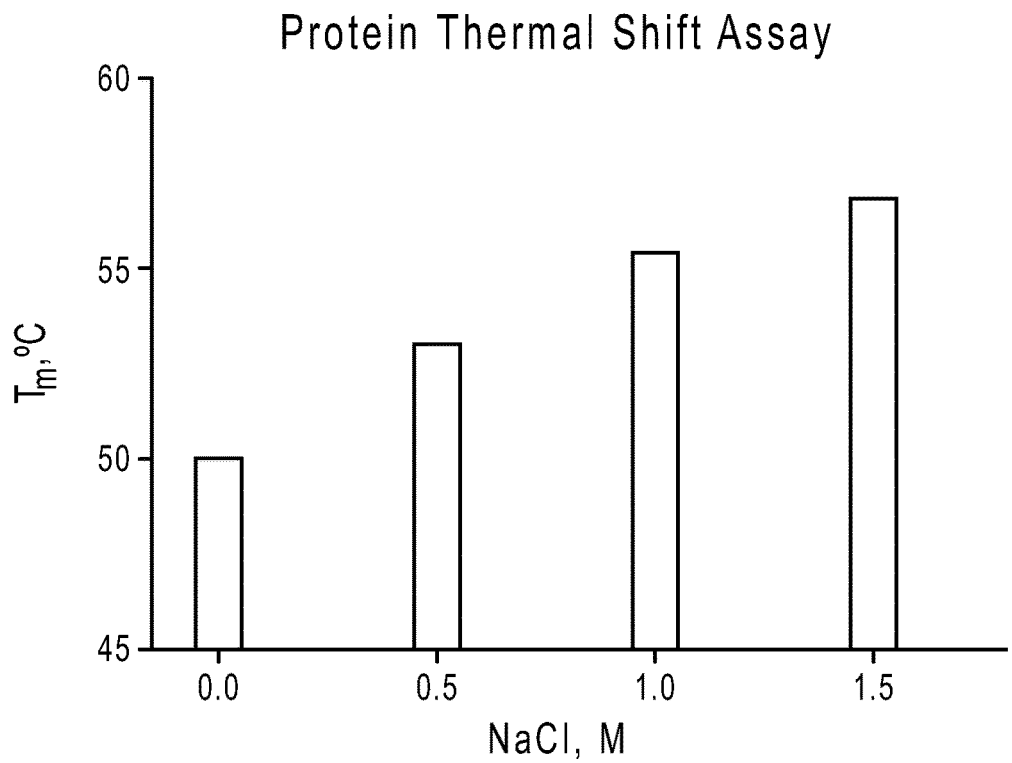
FIG. 1 shows MMLV H– RT melting temperature dependence on the concentration of NaCl as measured by a fluorescent protein thermal shift assay.

Table 1 provides a listing of certain sequences referenced herein.

TABLE 1

Description of the Sequences

| Description | Sequences | SEQ ID NO |
|---|---|---|
| Amino acid sequence of wildtype MMLV RT | TLNIEDEHRLHETSKEPDVSLGSTWLSDFPQAWAETGGM GLAVRQAPLIIPLKATSTPVSIKQYPMSQEARLGIKPHI QRLLDQGILVPCQSPWNTPLLPVKKPGTNDYRPVQDLRE VNKRVEDIHPTVPNPYNLLSGLPPSHQWYTVLDLKDAFF CLRLHPTSQPLFAFEWRDPEMGISGQLTWTRLPQGFKNS PTLFDEALHRDLADFRIQHPDLILLQYVDDLLLAATSEL DCQQGTRALLQTLGNLGYRASAKKAQICQKQVKYLGYLL KEGQRWLTEARKETVMGQPTPKTPRQLREFLGTAGFCRL WIPGFAEMAAPLYPLTKTGTLFNWGPDQQKAYQEIKQAL LTAPALGLPDLTKPFELFVDEKQGYAKGVLTQKLGPWRR PVAYLSKKLDPVAAGWPPCLRMVAAIAVLTKDAGKLTMG QPLVILAPHAVEALVKQPPDRWLSNARMTHYQALLLDTD RVQFGPVVALNPATLLPLPEEGLQHNCLDILAEAHGTRP DLTDQPLPDADHTWYT*D*GSSLLQEGQRKAGAAVTTETEV IWAKALPAGTSAQRAELIALTQALKMAEGKKLNVYTDSR YAFATAHIHGEIYRRRGLLTSEGKEIKNKDEILALLKAL FLPKRLSIIHCPGHQKGHSAEARGNRMADQAARKAAITE TPDTSTLLIENSSPNSRLIN | 1 |
| Amino acid sequence of MMLV H– RT with D524A mutation | TLNIEDEHRLHETSKEPDVSLGSTWLSDFPQAWAETGGM GLAVRQAPLIIPLKATSTPVSIKQYPMSQEARLGIKPHI QRLLDQGILVPCQSPWNTPLLPVKKPGTNDYRPVQDLRE VNKRVEDIHPTVPNPYNLLSGLPPSHQWYTVLDLKDAFF CLRLHPTSQPLFAFEWRDPEMGISGQLTWTRLPQGFKNS PTLFDEALHRDLADFRIQHPDLILLQYVDDLLLAATSEL DCQQGTRALLQTLGNLGYRASAKKAQICQKQVKYLGYLL KEGQRWLTEARKETVMGQPTPKTPRQLREFLGTAGFCRL WIPGFAEMAAPLYPLTKTGTLFNWGPDQQKAYQEIKQAL LTAPALGLPDLTKPFELFVDEKQGYAKGVLTQKLGPWRR PVAYLSKKLDPVAAGWPPCLRMVAAIAVLTKDAGKLTMG QPLVILAPHAVEALVKQPPDRWLSNARMTHYQALLLDTD | 2 |

TABLE 1-continued

Description of the Sequences

| Description | Sequences | SEQ ID NO |
|---|---|---|
| | RVQFGPVVALNPATLLPLPEEGLQHNCLDILAEAHGTRP DLTDQPLPDADHTWYTAGSSLLQEGQRKAGAAVTTETEV IWAKALPAGTSAQRAELIALTQALKMAEGKKLNVYTDSR YAFATAHIHGEIYRRRGLLTSEGKEIKNKDEILALLKAL FLPKRLSIIHCPGHQKGHSAEARGNRMADQAARKAAITE TPDTSTLLIENSSPNSRLIN | |

DESCRIPTION OF THE EMBODIMENTS

I. Definitions

As used herein, "automated liquid handling device" or "automated liquid handling system" refers to a robot or automation technology used to dispense and sample multiple liquids at one time. Glycerol may interfere with the performance of some automated liquid handling devices.

As used herein, "buffer salt" refers to any salt that fixes excess amounts of acid or alkali without a change in hydrogen ion concentration. Exemplary buffer salts include tris(hydroxymethyl)aminomethane (Tris) HCl, 4-(2-hydroxyethyl)-1-piperazineethanesulfonic acid (HEPES), Bis-Tris, Mes, and/or Mops. In some embodiments, more than one buffer salt may be used in a stabilized enzyme formulation.

As used herein, "cryoprotectant" refers to any substance used to protect samples from freezing damage and/or ice formation. Cryoprotectants are essential for freezing and thawing of biological solutions to maintain activity of agents in the solution. Exemplary cryoprotectants include sorbitol, mannose, arabinose, sucrose, rhamnose, mannitol, trehalose, xylose, maltose, raffinose, and/or innulin. In some embodiments, more than one cryoprotectant may be used in a stabilized enzyme formulation.

As used herein, "detergent" refers to any surfactant or any amphipathic molecules that contain both polar and hydrophobic groups. A "non-ionic detergent" refers to any detergent with an uncharged hydrophilic head groups. Non-ionic detergents can solubilize membrane proteins in a gentle manner and allow the solubilized proteins to retain native subunit structure, enzymatic activity, and/or nonenzymatic function. Exemplary non-ionic detergents include Triton X-100, Nonidet P-40, Tween 20, Tween 80, Brij 35, Brij 68, Tween 85, Synperonic® detergent, Hecameg® detergent, and/or Elugent™ detergent. In some embodiments, more than one detergent or non-ionic detergent may be used in a stabilized enzyme formulation.

As used herein, "enzyme" refers to any biological catalyst. Reverse transcriptases (RTs) are an exemplary class of enzymes. Enzyme may include MMLV RT wildtype and variants, AMV RT wildtype and variants, and HIV RT wildtype and variants. Enzymes may also include Superscript IV RT, AffinityScript Reverse Transcriptase, NxtScript Reverse Transcriptase, RnaUsScript Reverse Transcriptase, SensiScript RT, RocketScript Reverse Transcriptase, GoScript Reverse Transcriptase, and/or Thermoscript reverse transcriptase.

As used herein, "freeze-thaw" or "freeze-thawing" refers to a set of cycles of freezing a sample and returning it to room temperature. As enzyme activity is known to decrease over freeze-thaw cycles, the stability of a stabilized enzyme formulation may be assessed by freeze-thaw analysis.

As used herein, "glycerol-free" buffer, solution, or formulation refers to a buffer, solution, or formulation comprising not more than 2% glycerol. In some further embodiments, the buffer, solution, or formulation may comprise no glycerol, nominal glycerol, undetectable glycerol, not more than 1% glycerol, not more than 0.5% glycerol, and/or not more than 0.1% glycerol. However, in some embodiments, a glycerol-free buffer comprises a measurable amount of glycerol that is less than or equal to 2%.

As used herein, "high-throughput screening" or "HTS" refers to methods to process a large number of samples in an experiment. HTS methods might comprise robotics and/or automated liquid handling devices. Examples of HTS formats might experiments and equipment used with 384-well or 1536-well plates. Glycerol is known to interfere with aspects of HTS methods, such as automated liquid handling devices.

As used herein, "ionic strength" refers to the measure of the concentration of ions in solution. By ions, we refer only to the ions from the salt(s) in the glycerol free buffer providing Na+ and/or K+ ions, and not including any buffer salts. Ionic strength may be calculated according to the formula:

$$I = \frac{1}{2} \Sigma c_i z_i^2$$

Where $c_i$ is concentration of each type of ion (moles/liter), $z_i$ is charge of each type of ion. The ionic strength of a buffer is considered to be high if it is more than 0.25 M. If calculated according to the formula, 100 mM $Na_2SO_4$ or $K_2SO_4$ provide ionic strength of 0.3M, whereas for NaCl or KCl, 0.3M ionic strength is provided only at 300 mM salt concentration. Accordingly, the ionic strength provided by, for example, 300 mM of $Na_2SO_4$ or $K_2SO_4$ would be several times higher than the one provided by 300 mM of NaCl or KCl, and will thus provide much higher RT stability than Na or K chloride salts.

As used herein, "reducing agent" refers to any agent that loses an electron to another chemical species in a redox chemical reaction. In some embodiments, a reducing agent prevents denaturation of an enzyme, such as an RT. Exemplary reducing agents include mercaptoethanol, dithiothreitol (DTT), Tris-(carboxyethyl) phosphine hydrochloride (TCEP), n-acetyl-L-cysteine (NALC), or L-glutathione (in its reduced GSH glutathione and oxidized GSSG glutathione dioxide forms). In some embodiments, more than one reducing agent may be used in a stabilized enzyme formulation.

As used herein, "stability" refers to the retention by an enzyme of at least 70% of activity after the enzyme or composition containing the enzyme has been stored either for at least 5 days at 25° C. or at least 4 months at −20° C. In some further embodiments, the enzyme retains at least 80% or at least 90% of the original enzymatic activity (in units) after the enzyme or composition containing the enzyme has been stored for at least 5 days at 25° C. or at least 4 months at −20° C.

As used herein, a "stabilized enzyme formulation" refers to an enzyme in a solution comprising one or more stabilizer. A stabilized enzyme formulation may therefore have greater stability than a non-stabilized formulation. A stabilized enzyme formulation may also refer to a lyophilized product generated from a solution comprising one or more stabilizer.

As used herein, a "stabilizer" or "stabilizing agent" is an agent that improves the stability of an enzyme formulation. In some embodiments, the stabilizer(s) comprise arginine, $MgCl_2$, $MgSO_4$, PEG, TMAO (trimethylamine N-oxide), and/or PVP (polyvinyl-pyrrolidone). For example, an enzyme in a formulation with a stabilizing agent may display greater relative activity over a particular incubation (for example, a certain amount of time at a certain temperature) compared to an enzyme in a formulation without the stabilizing agent. In some embodiments, more than one stabilizer may be used in a stabilized enzyme formulation.

As used herein, "unit range" or "unit ranges" refers to the amount of enzyme in units per microliter (U/μL) that may be employed herein. In some embodiments, acceptable unit ranges include from 20-600 U/μL. In some embodiments, enzymes may be more stable at higher enzyme concentrations such as from 200-300 U/μL, 300-600 U/μL, 400-600 U/μL, or 500-600 U/μL.

As used herein, "reverse transcriptase" or "RT" refers to an enzyme that can generate complementary DNA from an RNA template. An RT may refer to any enzyme that can perform reverse transcription. Exemplary RTs include wild-type MMLV RT (SEQ ID NO: 1), MMLV H− RT (SEQ ID No: 2), RevertAid RT, Maxima RT, Superscript III RT, Superscript IV RT, AffinityScript Reverse Transcriptase, NxtScript Reverse Transcriptase, RnaUsScript Reverse Transcriptase, SensiScript RT, RocketScript Reverse Transcriptase, GoScript Reverse Transcriptase, and/or Thermoscript reverse transcriptase.

A "mutant RT," "mutant enzyme," or "mutant MMLV" refers to an enzyme with an amino acid change from the wild-type sequence. This amino acid change in the mutant enzyme may be any amino acid change such as an amino acid substitution, deletion, or insertion. In some embodiments, a mutant MMLV has a measurable difference in structure or function compared to the wild-type enzyme. In some embodiments, a mutant MMLV has greater thermostability (i.e., ability to catalyze a reaction at temperatures above 37° C.). For example, wild-type MMLV RT possesses both DNA-dependent polymerase activity and RNase H activity. The RNase H activity degrades RNA from RNA-DNA duplexes for efficient double-stranded DNA synthesis. However, use of RT with RNase H activity may not be desired for use with long mRNA templates, as truncated cDNA may be formed if RNA is degraded prematurely by RNase H activity. Thus, commercial RTs are available that possess or lack RNase activity, which may denoted as RNase H+ or RNase H− enzymes. An RNase H− enzyme may be considered a mutant MMLV. Exemplary mutant RTs include RevertAid RT, Maxima RT, Superscript III RT, and SuperScript IV RT.

In some embodiments, a mutant MMLV RT is a reverse transcriptase which is 70%, 75%, 80%, 85%, 90%, 95%, 96%, 97%, 98%, or 99% identical at the amino acid level to a reverse transcriptase comprising the amino acid sequence SEQ ID NO:1.

II. Stabilized Enzyme Formulations

This disclosure relates to stabilizing effect of high concentrations of salts providing Na+ and/or K+ ions and stabilized enzyme formulations. In some embodiments, the enzyme is a reverse transcriptase (RT). In some embodiments, the enzyme is MMLV. In some embodiments, the MMLV is MMLV H+ or MMLV H−. In some embodiments, the MMLV is a wildtype sequence, such as SEQ ID NO: 1. In some embodiments, the MMLV is a mutant MMLV. In some embodiments, the mutant MMLV is an MMLV H− RT with D524A mutation, such as SEQ ID NO: 2. In some embodiments, the mutant MMLV is RevertAid, Maxima, Superscript III or SuperScript IV. In some embodiments, the concentration of enzyme in the formulation is from 180 to 220 units/μL.

Stabilized enzyme formulations described herein enable storage of MMLV H-reverse transcriptase enzyme in a glycerol-free buffer environment without losing structure integrity and catalytic activity. Similar results are expected for other MMLV enzymes, other reverse transcriptases, and also enzymes generally. These stabilized enzyme formulations incorporate the unexpected stabilizing effect of MMLV H− reverse transcriptase by $Na^+$ and $K^+$ cation-providing salts and $Cl^-$ and $SO_4^{-2}$ anion-providing salts (including NaCl, $Na_2SO_4$, KCl, and $K_2SO_4$), which was presently discovered during thermal stability studies using fluorescent protein thermal shift assay. The stabilizing effect of MMLV H− reverse transcriptase was, in the present work, subsequently empirically proven by evaluating the residual catalytic activities of target enzyme after pre-incubation under various temperature regimes in the presence of different concentrations of $K^+$ and $Na^+$ based salts.

Previously disclosed RT storage buffers were based on glycerol's stabilizing effect and generally comprise salts (NaCl), a reducing agent, a chelating agent, a non-ionic detergent, and glycerol. One such previously-described RT storage buffer with glycerol would be 20-50 mM Tris-HCl (pH 7.5), 100-200 mM NaCl, 1-10 mM DTT, 0.1-1 mM ethylenediaminetetraacetic acid (EDTA), and 0.01%-0.1% non-ionic detergent (e.g., Triton X-100 or Nonidet P-40), and 50% glycerol.

Stabilized enzyme formulations disclosed herein are glycerol-free. In some embodiments, a glycerol-free solution has no glycerol. In some embodiments, a glycerol-free solution has nominal glycerol or glycerol that is undetectable. In some embodiments, a glycerol-free buffer comprises no more than 2% glycerol. In some embodiments, a glycerol-free buffer comprises no more than 1% glycerol. In some embodiments, a glycerol-free buffer comprises no more than 0.5% glycerol. In some embodiments, a glycerol-free buffer comprises no more than 0.1% glycerol.

A. Salt Components

Stabilized enzyme formulations disclosed herein comprise one or more salts providing Na+ and/or K+ ions at concentration of at least 300 mM. In some embodiments, the salt(s) providing Na+ and/or K+ ions comprise NaCl, KCl, $Na_2SO_4$, and/or $K_2SO_4$. In some embodiments, the salt(s) providing Na+ and/or K+ ions comprise a sulfate salt. In some embodiments, the salt(s) providing Na+ and/or K+ ions comprise $Na_2SO_4$ and/or $K_2SO_4$.

In some embodiments, the formulation comprises at least a 300 mM concentration of salt(s) providing Na+ and/or K+ ions. In some embodiments, the formulation comprises at least a 500 mM concentration of salt(s) providing Na+ and/or K+ ions. In some embodiments, the formulation comprises at least a 1000 mM concentration of salt(s) providing Na+ and/or K+ ions. In some embodiments, the formulation comprises at least a 1500 mM concentration of salt(s) providing Na+ and/or K+ ions. In some embodiments, the formulation comprises from a 300 mM to 1500 mM concentration of salt(s) providing Na+ and/or K+ ions. In some embodiments, the formulation comprises from 400 mM to 1500 mM, 500 mM to 1500 mM, or 1000 mM to 1500 mM concentration of salt(s) providing Na+ and/or K+ ions. In some embodiments, the formulation comprises at least 100 mM, 200 mM, 300 mM, 400 mM, 500 mM, 600 mM, 700 mM, 800 mM, 900 mM, 1000 mM, 1100 mM, 1200 mM, 1300 mM, 1400 mM, or 1500 mM concentration of salt(s) providing Na+ and/or K+ ions. In some embodiments, the formulation comprises at least 100 mM, 200 mM, 300 mM, 400 mM, 500 mM, 600 mM, 700 mM, 800 mM, 900 mM, 1000 mM, 1100 mM, 1200 mM, 1300 mM, 1400 mM, or 1500 mM concentration of salt(s) providing Cl⁻ ions and Na+ and/or K+ ions. In some embodiments, the formulation comprises at least 100 mM, 200 mM, 300 mM, 400 mM, 500 mM concentration of salt(s) providing $SO_4^{2-}$ ions and Na+ and/or K+ ions.

In some embodiments, the formulation comprises from a 100 mM to 1500 mM concentration of salt(s) providing K+ ions. In some embodiments, the formulation comprises from a 300 mM to 1500 mM concentration of salt(s) providing Na+ ions.

In some embodiments, the amount of salt is sufficient to increase the melting temperature of the enzyme. For example, the melting temperature may be increased by 0.5° C., 1° C., 2° C., 3° C., 4° C., or 5° C., as compared to the same enzyme in a control buffer of 50 mM Hepes pH 7.0, 6.7 mM NaCl, 0.1 mM DTT, 0.27% sucrose, and 0.007 mM EDTA. In some embodiments, the melting temperature is increased by 0.5° C. to 5° C., 0.5° C. to 3° C., or by 1 to 3° C., as compared to the same enzyme in a control buffer of 50 mM Hepes pH 7.0, 6.7 mM NaCl, 0.1 mM DTT, 0.27% sucrose, and 0.007 mM EDTA. Increasing melting temperature shows increased stabilization of the enzyme.

The amount of salt may also be expressed using the ionic strength of the buffer. As shown in Example 3 the stability of RT in the glycerol-free storage buffer is believed due to high ionic strength of the buffer, that is provided by selected salts. The results correlate with the theoretical calculation of ionic strength according to the formula:

$$I = \frac{1}{2} \Sigma c_i z_i^2$$

Where $c_i$ is concentration of each type of ion (moles/litre), $z_i$ is charge of each type of ion. The ionic strength of a buffer is considered to be high if it is more than 0.25 M. If calculated according to the formula, 100 mM $Na_2SO_4$ or $K_2SO_4$ provide ionic strength of 0.3M, whereas for NaCl or KCl, 0.3M ionic strength can be calculated only at 300 mM salt concentration. Accordingly, the ionic strength provided by, for example, 300 mM of $Na_2SO_4$ or $K_2SO_4$ would be several times higher than the one provided by 300 mM of NaCl or KCl, and will thus provide much higher RT stability than Na or K chloride salts. In some embodiments, the ionic strength of the buffer may be 0.25M, 0.3 M, 0.35M, 0.4M, 0.5M, 0.6M, 0.7M, 0.8M, 0.9M, 1.0M, 1.1M, 1.2M, 1.3M, 1.4M, or 1.5M, or higher. In some embodiments, the ionic strength of the buffer may be from 0.25M to 1.5M, from 0.3M to 1.5M, from 0.3M to 0.5M, from 0.5M to 1.0M, or from 1.0M to 1.5M. In some embodiments, the ionic strength of the buffer may be from 0.5 to 1.5 M.

B. Other Components

In some embodiments, the stabilized enzyme formulation further comprises at least one of a buffer salt(s); reducing agent(s); detergent(s); cryoprotectant(s); and/or optional other stabilizer(s).

In some embodiments, the stabilized enzyme formulation comprises one or more buffer salt(s). In some embodiments, the buffer salt(s) comprises Tris-HCl, HEPES, Bis-Tris, Mes, or Mops. In some embodiments, the concentration of buffer salts is from 10-100 mM, from 10-50 mM, from 50-100 mM, from 25 to 75 mM.

In some embodiments, the formulation has a pH from 6 to 8. In some embodiments, the pH of the formulation is 7.0, 7.5.

In some embodiments, the stabilized enzyme formulation comprises one or more reducing agent(s). In some embodiments, the reducing agent(s) comprises mercaptoethanol, DTT (1-20 mM), TCEP (0.1-20 mM), NALC (1-20 mM), and/or GSH/GSSG (1-20 mM). In some embodiments, the concentration of reducing agent(s) is 1-20 mM.

In some embodiments, the stabilized enzyme formulation comprises one or more detergent(s). In some embodiments, the detergent(s) is a non-ionic detergent(s). In some embodiments, the detergent(s) comprises Triton X-100, Nonidet P-40, Tween 20, Tween 80, Brij 35, Brij 68, Tween 85, Synperonic® detergent, Hecameg® detergent, and/or Elugent™ detergent. In some embodiments, the concentration of detergent(s) is 0.1 to 1%.

In some embodiments, the stabilized enzyme formulation comprises a one or more cryoprotectant(s). In some embodiments, the cryoprotectant(s) is sorbitol, mannose, arabinose, sucrose, rhamnose, mannitol, trehalose, xylose, maltose, raffinose, and/or innulin. In some embodiments, the cryoprotectant is sorbitol. In some embodiments, the formulation comprises 20% sorbitol. In some embodiments, the concentration of cryoprotectant(s) is 1%-25%.

In some embodiments, the stabilized enzyme formulation comprises other stabilizers. In some embodiments, the other stabilizer(s) comprise arginine (in some modes, 0.1-1 M), $MgCl_2$ (in some modes, 1-10 mM), $MgSO_4$ (in some modes, 1-10 mM), TMAO (trimethylamine N-oxide) (in some modes, 0.1-1 M), PVP (polyvinyl-pyrrolidone) (in some modes, 0.1-2%), glycine (in some modes, 0.1-1 M), cysteine (in some modes, 0.1-1M), PVA (polyvinyl alcohol) (in some modes, 0.1-2%), PEG4000 (in some modes, 1-10%), PEG8000 (in some modes, 1-10%), Ficoll (in some modes, 1-10%).

In some embodiments, the glycerol-free buffer does not comprise amino acids. In some embodiments, the glycerol-free buffer does not comprise peptides. In some embodiments, the enzyme is the only peptide in the stabilized enzyme formulation. In some embodiments, the stabilized enzyme formulation comprises other proteins than the enzyme, for example antibodies, such as those capable of inhibiting the enzyme to provide for a "hot start" version of the enzyme, or other proteins. In some embodiments, the glycerol-free buffer does not comprise arginine. In some embodiments, the glycerol-free buffer does not comprise 20% arginine. In some embodiments, the glycerol-free buffer does not comprise poly(amino acid).

Table 2 provides some exemplary components that may be comprised in a stabilized enzyme formulation, such as salts providing Na+ and/or K+ ions, buffer salts, reducing agents, cryoprotectants, and other stabilizers. One skilled in the art would be aware of additional examples for each type of component. Further, a stabilized enzyme formulation need not have all components listed in Table 2, as long as the formulation comprises a glycerol-free buffer comprising at least a 300 mM concentration of salt(s) providing Cl− ions and Na+ and/or K+ ions or comprising at least a 100 mM concentration of salt(s) providing $SO_4^{2-}$ ions and Na+ and/or K+ ions and a buffer salt that provides a stable pH.

TABLE 2

Exemplary components of a stabilized enzyme formulation

| Components | Examples | Exemplary concentrations |
|---|---|---|
| Salts providing Na+ and/or K+ ions | NaCl, KCl, | 300-1500 mM |
| | $Na_2SO_4$, and/or $K_2SO_4$ | 100-500 mM |
| Buffer salts | Tris-HCl, HEPES, Bis-Tris, Mes, and/or Mops | 10-100 mM, including 10, 20, 30, 40, 50, 60, 70, 80, 90, or 100 mM pH 7, 7.5 |
| Reducing agents | Mercaptoethanol, DTT, NALC, and/or GSH/GSSG | 1-10 mM, including 1, 5, 10 mM for Mercaptoethanol, DTT, NALC, and/or GSH/GSSG |
| | TCEP | 0.1-5 mM, including 0.1, 0.2, 0.5, 1, 5 mM for TCEP |
| Detergent | Triton X-100, Nonidet P-40, Tween 20, Tween 80, Brij 35, and/or Brij 68 | 0.1-0.7%, including 0.1%, 0.2%, 0.5%, 0.7% |
| Cryoprotectants | Sorbitol, mannose, arabinose, sucrose, and/or rhamnose | 15-25%, including 15%, 20%, 25% sorbitol |
| Other stabilizers | Arginine, TMAO (trimethylamine N-oxide) | 0.1-1M, including 0.1M, 0.2M, 0.5M, 0.7M, 1M |
| | $MgCl_2$, $MgSO_4$, | 2-7 mM, including 2 mM, 5 mM, 7 mM |
| | PEG and/or PVP (polyvinyl-pyrrolidone) | 1-10%, including 1%, 2%, 5%, 7%, 10% 0.1-2%, including 0.1%, 0.5%, 1%, 1.5%, 2%. |

In some embodiments, the stabilized enzyme formulation retains activity during storage. In some embodiments, the stabilized enzyme formulation retains at least 70% activity after storage for at least 5 days at 25° C. and/or at least 4 months at −20° C. In some embodiments, the stabilized enzyme formulation maintains stability after at least 20 freeze-thaw cycles. In some embodiments, the stabilized enzyme formulation retains at least 70% activity after at least 20 freeze-thaw cycles.

In some embodiments, the stabilized enzyme formulation retains at least 80% activity after storage for at least 5 days at 25° C. and/or at least 4 months at −20° C. In some embodiments, the stabilized enzyme formulation retains at least 80% activity after at least 20 freeze-thaw cycles.

In some embodiments, the stabilized enzyme formulation retains at least 90% activity after storage for at least 5 days at 25° C. and/or at least 4 months at −20° C. In some embodiments, the stabilized enzyme formulation retains at least 90% activity after at least 20 freeze-thaw cycles.

III. Lyophilized Compositions

Lyophilization (also known as freeze-drying or cryodessication) can improve preservation of a perishable material or improve ease of transport.

For enzymes formulations, however, lyophilization may be prohibited by glycerol present as a stabilization agent. As such, stabilized glycerol-free enzyme formulations may have the advantage of being lyophilizable in comparison to formulations with glycerol. These compositions also have increased stability prior to lyophilization.

In some embodiments, stabilized enzyme formulations described herein may be lyophilized. Any means of lyophilization may be used, such as freezing and incremental steps in temperature back to 4° C. under vacuum pressure.

In some embodiments, a lyophilized formulation may be reconstituted back to a stabilized enzyme formulation by addition of water.

In some embodiments, a reconstituted lyophilized stabilized enzyme formulation retains at least 50% activity compared with unlyophilized sample. In some embodiments, a reconstituted lyophilized stabilized enzyme formulation retains at least 60% activity compared with unlyophilized sample. In some embodiments, a reconstituted lyophilized stabilized enzyme formulation retains at least 70% activity compared with unlyophilized sample. In some embodiments, a reconstituted lyophilized stabilized enzyme formulation retains at least 80% activity compared with unlyophilized sample. In some embodiments, a reconstituted lyophilized stabilized enzyme formulation retains at least 90% activity compared with unlyophilized sample.

IV. Methods of Use

Described herein is a method of stabilizing an enzyme formulation comprising providing the enzyme and glycerol-free buffer and allowing the glycerol-free buffer to stabilize the enzyme.

Also described herein is a method of storing a stabilized enzyme formulation comprising providing the stabilized enzyme formulation and storing the enzyme formulation for at least 5 days at 25° C. and/or at least 4 months at −20° C., wherein the stabilized enzyme formulation retains at least 70% activity after storage. In some embodiments, the stabilized enzyme formulation retains at least 80% activity after storage. In some embodiments, the stabilized enzyme formulation retains at least 90% activity after storage.

In some embodiments, the storage is for at least 5 days at 25° C. In some embodiments, the storage is for at least 24 days at 25° C.

In some embodiments, the storage is for at least 4 months at −20° C. In some embodiments, the storage is for at least 18 months at −20° C.

Also described herein is a method of producing complementary DNA (cDNA) from an RNA sample comprising obtaining an RNA sample; mixing the sample with one or more primer, deoxynucleotide triphosphates (dNTPs), and a stabilized enzyme formulation described herein; and incubating the mixture in reaction buffer. In some embodiments, the cDNA produced may be used for a subsequent separate reaction. In some embodiments, the cDNA produced is added to a separate PCR reaction, in a two-step PCR protocol. In some embodiments, the cDNA produced may be used directly from the reaction mixture without further purification. In some embodiments, the cDNA produced is used for a subsequent PCR reaction in the same reaction tube (one-step PCR). In some embodiments, the stabilized enzyme formulation may benefit from dilution, depending on the unit concentration of enzymes, the concentration of salts, and the application of interest for the enzyme.

In some embodiments, a stabilized enzyme formulation is diluted with water or buffer before mixing with the RNA sample.

In some embodiments, polymerase chain reaction (PCR) methods are used after producing the cDNA, as either a one-step or two-step PCR protocol. PCR reactions are techniques used to amplify a single copy or a few copies of a segment of DNA across several orders of magnitude. A wide variety of PCR methods would be known to one skilled in the art including sequencing, DNA profiling, diagnosis of hereditary disease, or detection of pathogens.

In some embodiments, the PCR methods are done following termination of the reaction in a two-step reverse transcription-PCR reaction.

In some embodiments, the cDNA is stored for later use. In some embodiments, the complementary DNA is stored at −20° C. or lower for later use.

In some embodiments, wherein the one or more primer is non-specific. In some embodiments, the one or more non-specific primer is an oligo(dT)$_{18-20}$ (SEQ ID NO: 3) or a random hexamer primer.

In some embodiments, the one or more primer is gene-specific.

In some embodiments, the RNA is total RNA, poly(A) RNA, or specific RNA.

In some embodiments, the reaction buffer comprises RNase inhibitor. An RNase inhibitor reduces breakdown of the RNA.

In some embodiments, the incubating in reaction buffer is at between 50° C.-70° C. In some embodiments, the incubating in reaction buffer is for 10-30 minutes.

In some embodiments, the terminating is done by heating at 85° C.

In some embodiments, the method is used in a high-throughput screening format. In some embodiments, the method is used with automated liquid handling devices. In some embodiments, the method is used for single cell mRNA sequencing.

Depending on the usage concentration of enzyme, and concentration of salts, the stabilized composition is convenient to store and transport. In some embodiments, it may be diluted before use. In other embodiments, it may be used without dilution.

In some embodiments, 200U of RT enzyme is added to the 20 ul reaction with RNA amounts from 1 pg-1 μg total RNA, 0.1 pg-500 ng mRNA, or 0.01 pg-500 ng specific RNA.

EXAMPLES

Example 1: Demonstration of Reverse Transcriptase MMLV H− Thermal Stability

Fluorescent thermal shift assay reliably reports any change as significant when the difference between protein melting temperatures are below the determined experimental error which is typically below 2° C. (Boivin S., Kozak S., Meijers R. Optimization of protein purification and characterization using Thermofluor screens. Protein Expression and Purification, 2013). The thermal shift assays of MMLV H− RT were performed with a range of stabilizing conditions and compounds such as pH, salts, reducing agents, detergents, and cryoprotectants. It was surprisingly found that increased concentrations of NaCl in the storage buffer provided significant increase of MMLV H− RT melting temperature (see FIG. 1). For example, the presence of 0.5 M of NaCl increased the melting temperature of reverse transcriptase by as much as 3° C.

This example evaluated reverse transcriptase MMLV H− thermal stability using melting temperature [Tm] change in relation to increasing concentrations of NaCl.

Fluorescence protein thermal shift experiments were performed on a qPCR machine Rotor-Gene 6000. Fluorescent signal was detected by using excitation channel at 365±20 nm and emmission at 460±15 nm. Reporter fluorescent dye was 8-anilino-1-naphthalenesulfonic acid ammonium salt used at a concentration of 50-100 μM. 1-2 μg of MMLV H− RT enzyme was added to the 10-15 μl per single reaction (buffer composition: 50 mM Hepes pH 7.0, 6.7 mM NaCl, 0.1 mM DTT, 0.27% sucrose, 0.007 mM EDTA+ reverse transcriptase+varying amounts of tested components). Samples are heated at a rate of 1° C./min from 25° C. to 99° C. Data was analyzed by using a ThermoFluor++ software wherein Tm values were calculated.

FIG. 1 shows increased melting temperature for MMLV H− RT at various concentrations of NaCl in the buffer. This demonstrates that increasing the NaCl concentration in the storage buffer improved thermal stability of the MMLV H− RT.

Example 2: Demonstration of NaCl Effect on Stability and Activity of MMLV H− RT

The residual specific activity of the target enzyme (MMLV H− RT) was evaluated after incubation for 5 days at the room temperature (25° C.) in the formulation a buffer of 50 mM Tris pH 7.5, 1 mM EDTA, 5 mM DTT, 0.1% Triton X-100 and NaCl ranging from 100 mM to 1500 mM, respectively. Storage for 5 days at 25° C. corresponds to roughly 4 months of stability at −20° C. The experimental data confirmed that increased concentrations of NaCl significantly stabilized MMLV H− RT in formulations without glycerol.

More specifically, in this experiment, glycerol was removed from MMLV H− RT enzyme by using a cation exchange chromatography (SP Sepharose FF, GE Healthcare), and the enzyme was dialyzed into a final storage buffer which contained the following composition: 50 mM Tris-Cl pH 7.5, 5 mM DTT, 1 mM EDTA, 0.1% Triton X-100 and 100-1500 mM of NaCl. The remaining amount of glycerol was about or less than 0.1%. All experiments were performed with MMLV H− RT samples having an activity of 200±20 units/μl.

To evaluate MMLV H− RT stability the protein was incubated for 5 days at 25° C. and its activity has been measured using the following assay: [3H]-dTTP incorporation into poly(A)-oligo(dT)18 ("(dT)18" disclosed as SEQ ID NO: 4) substrate has been measured in a 20 μl reaction composed of 0.4 mM poly(A)-oligo(dT)18 ("(dT)18" disclosed as SEQ ID NO: 4), 0.4 MBq/ml [3H]-dTTP, 0.5 mM dTTP, 1× RT reaction buffer (50 mM Tris-Cl pH 8.3, 50 mM KCl, 4 mM MgCl$_2$, 10 mM DTT) and 5 μl of reverse transcriptase diluted with a dilution buffer (30 mM Tris-HCl pH 8.3, 10 mM DTT, 0.5 mg/ml BSA, 0.02% Triton X-100) to 0.1 U/μl. The reaction was incubated at 37° C. for 10 min and the reaction was terminated by cooling the samples in the ice box. The radioactive product (18 μl of the total reaction) was adsorbed onto the nylon membranes which were dried under the IR lamp (10 min) and subsequently washed with 7.5% Na$_2$HPO$_4$ pH 6.5 solution, water and acetone. Then membranes were dried under the IR lamp, and immersed into the scintillation vials containing 5 ml of scintillation fluid (Betaplate Scint). Radioactivity was measured by using a scintillation counter and activity units of each sample was calculated by using a control sample of 200 U/μl. 1 unit of activity was recorded as the amount of enzyme necessary to catalyze the incorporation of 1 nmol dTTP into poly(A)-oligo(dT)18 ("(dT)18" disclosed as SEQ ID NO: 4) substrate at 37° C. in 10 min. Relative activity was calculated as the percentage of activity of the enzyme after incubation for 5 days at 25° C. compared with an unincubated sample.

Figure 2:
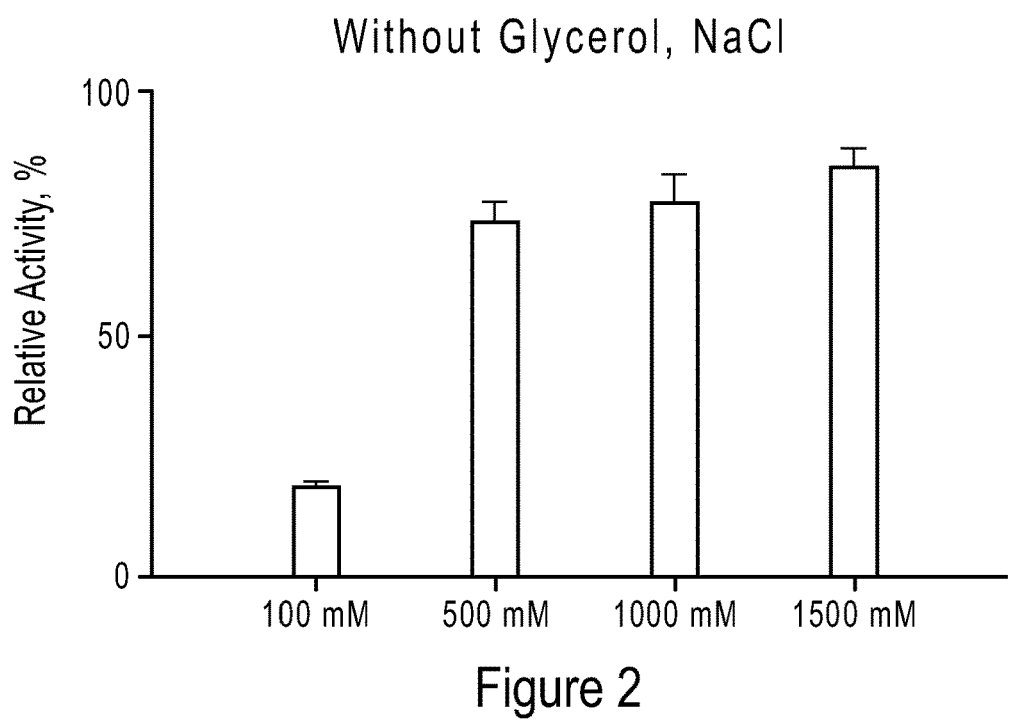
FIG. 2 shows MMLV H– RT activity dependence in relation to concentration of NaCl after enzyme incubation for 5 days at 25° C. NaCl concentration was increased from 100 mM up to 1500 mM in glycerol-free buffer containing 50 mM Tris-Cl pH 7.5, 5 mM DTT, 1 mM EDTA and 0.1% Triton X-100. Relative activity is provided in percentage that is the ratio of incubated and unincubated sample for 5 days at 25° C., corresponding approximately to 4 months when stored at −20° C. Unincubated sample is the initial sample right after the formulation of the enzyme having an activity of 200±20 units/4 μl.

FIG. 2 shows that the relative activity (%) of MMLV H− RT increased with higher levels of NaCl in a buffer without glycerol over the range 100 nM to 1500 nM NaCl.

Example 3: Demonstration of KCl, Na$_2$SO$_4$, or K$_2$SO$_4$ Effects on Stability and Activity of MMLV H– RT It was suggested that the increased stability of reverse transcriptase might be not due to the presence of increased amounts of a specific salt, but rather because of the increased ionic strength of the storage buffer. Therefore, other salts were selected to investigate their influence on RT stability: KCl (100 mM or 1000 mM), K$_2$SO$_4$ (100 mM or 500 mM), and Na$_2$SO$_4$ (100 mM or 500 mM). In this example, significant stabilization of RT enzyme (>70% of activity) was observed already in the presence of 100 mM Na$_2$SO$_4$ or 100 mM K$_2$SO$_4$, whereas the 100 mM KCl in the storage buffer provided only for about 20% residual RT activity. The effect of various concentrations of KCl correspond to the stabilization effect of another chloride salt—NaCl from Example 2.

The results confirmed our postulation that the stability of RT in the glycerol-free storage buffer is due to high ionic strength of the buffer, that is provided by selected salts. The experimental results correlate to some extent with the theoretical calculation of ionic strength according to the formula for ionic strength:

$$I = \tfrac{1}{2}\Sigma c_i z_i^2$$

Where $c_i$ is concentration of each type of ion (moles/liter), $z_i$ is charge of each type of ion.

The ionic strength of a buffer is considered to be high if it is more than 0.25 M. If calculated according to the formula, 100 mM Na$_2$SO$_4$ or K$_2$SO$_4$ provide ionic strength of 0.3M, whereas for NaCl or KCl, 0.3M ionic strength can be calculated only at 300 mM salt concentration. Accordingly, the ionic strength provided by, for example, 300 mM of Na$_2$SO$_4$ or K$_2$SO$_4$ would be several times higher than the one provided by 300 mM of NaCl or KCl, and will thus provide much higher RT stability than Na or K chloride salts.

From the experiments, it can be seen that where the ionic strength of glycerol-free RT storage buffer is 0.5 M and more, the stability of RT is >70% activity after incubation for 5 days at 25° C.

Figure 3:
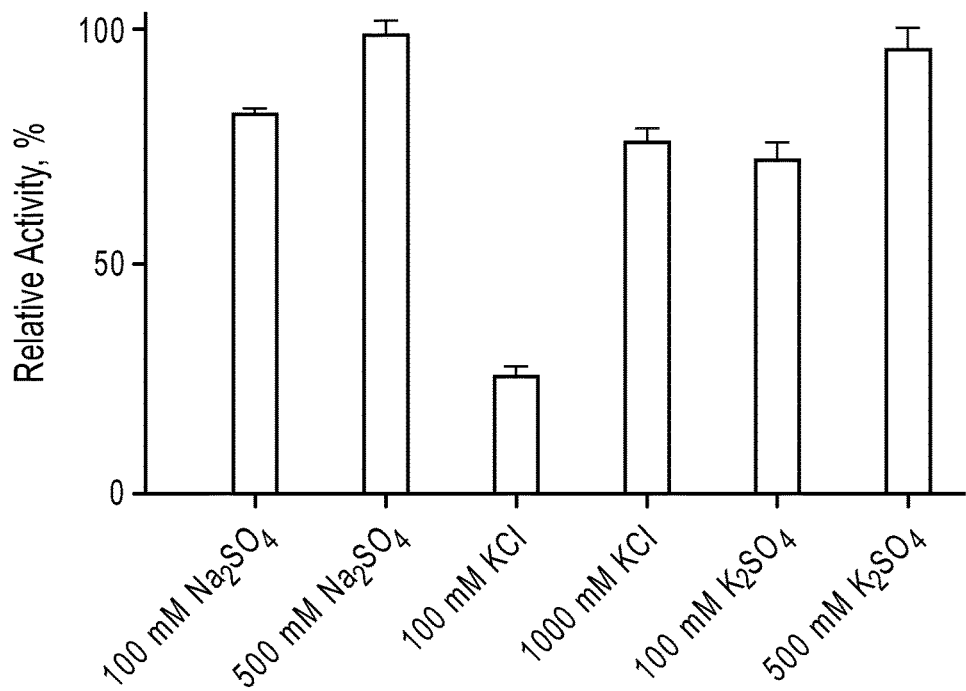
FIG. 3 illustrates KCl, $Na_2SO_4$ and $K_2SO_4$ effect on the stability of MMLV H– RT. Enzyme has been incubated for 5 days at +25° C. in the presence of different salts and its activity has been measured. Different salt concentrations as shown in the figure were supplemented to the basic buffer containing 50 mM Tris-Cl pH 7.5, 5 mM DTT, 1 mM EDTA, and 0.1% Triton X-100.

The residual specific activity of the target enzyme was evaluated after incubation for 5 days at the room temperature a buffer of 50 mM Tris pH 7.5, 1 mM EDTA, 5 mM DTT, 0.1% Triton X-100 and a salt providing Na+ or K+ ion. KCl (100 mM or 1000 mM), K$_2$SO$_4$ (100 mM or 500 mM), or Na$_2$SO$_4$ (100 or 500 mM) were tested. The procedures followed those of Example 2 except for differences noted here. The experimental data in FIG. 3 shows that KCl or Na+ or K+ sulfates stabilized MMLV H– RT during 5 days of incubation at the room temperature. FIG. 3 also shows that RT stabilization may be salt dependent, as MMLV H– RT was more stabilized by salts containing divalent anions, such as —SO$_4^{2-}$.

Example 4: Demonstration of NaCl or Na$_2$SO$_4$ Effect on Stability and Activity of MMLV H– in the Presence of 50% Glycerol The effect of NaCl or Na$_2$SO$_4$ on the stability of MMLV H– RT was also tested in the presence of 50% glycerol. Enzyme was incubated for 5 days at +25° C. in the presence of different salts and its activity was measured. 100 mM and 1000 mM of NaCl or 100 mM and 500 mM of Na$_2$SO$_4$ were added to the glycerol-containing buffer containing 50 mM Tris-Cl pH 7.5, 5 mM DTT, 1 mM EDTA and 0.1% Triton X-100, and 50% glycerol.

The residual activity of target enzyme was measured after 5 days of incubation at room temperature. The procedures of Example 2 were conducted except for differences noted here.

Figure 4:
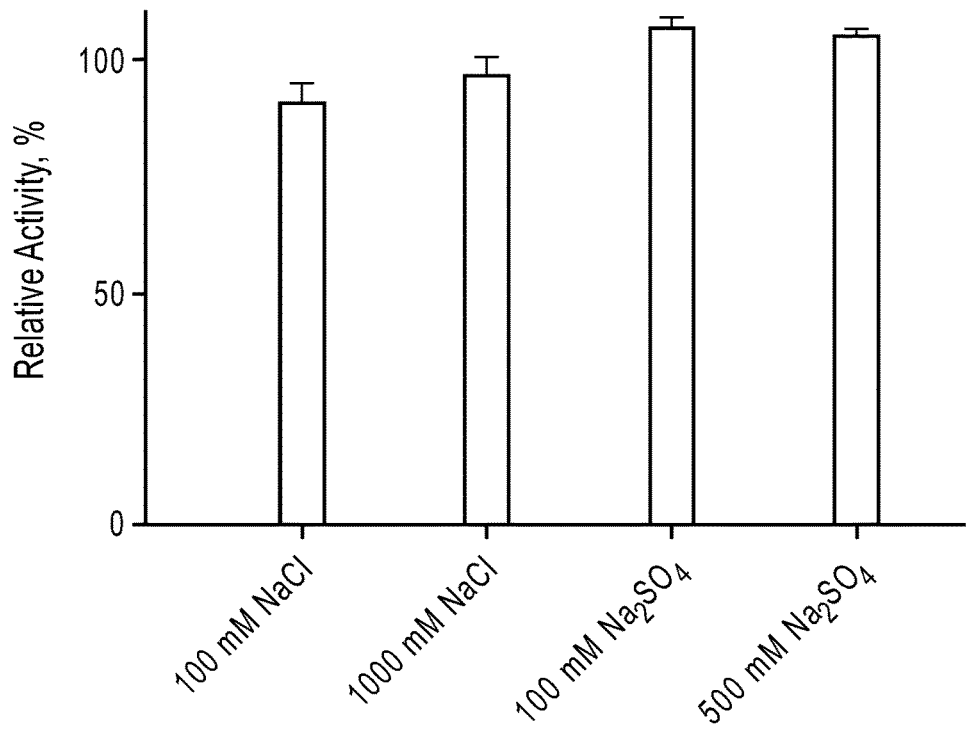
FIG. 4 illustrates NaCl- and $Na_2SO_4$-dependent effects on the stability of MMLV H– RT in the presence of 50% glycerol. Enzyme was incubated for 5 days at +25° C. in the presence of different salts, and its activity was measured. 100 mM and 1000 mM of NaCl or 100 mM and 500 mM of $Na_2SO_4$ were added to the glycerol buffer containing 50 mM Tris-Cl pH 7.5, 5 mM DTT, 1 mM EDTA and 0.1% Triton X-100, and 50% glycerol.

FIG. 4 shows higher salt concentration had a reduced effect on stabilizing RT in the presence of glycerol. This supports the role of high salt concentration as a potential substitute for glycerol for long-term preservation of RT enzymes.

Example 5: Demonstration of NaCl or Na$_2$SO$_4$ Effect on Stability and Activity of MMLV H– in the Presence of 20% of Sorbitol The effects of NaCl and Na$_2$SO$_4$ concentrations on the stability of MMLV H– RT was tested in the presence of 20% sorbitol. Enzyme was incubated for 5 days at +25° C. in the presence of different salts and its activity was measured. 100 mM and 1000 mM of NaCl or 100 mM and 500 mM of Na$_2$SO$_4$ was added to the sorbitol buffer containing 50 mM Tris-Cl pH 7.5, 5 mM DTT, 1 mM EDTA and 0.1% Triton X-100, and 20% sorbitol.

The residual activity of target enzyme was measured after 5 days at the room temperature. The procedures of Example 2 were conducted except for differences noted here.

Figure 5:
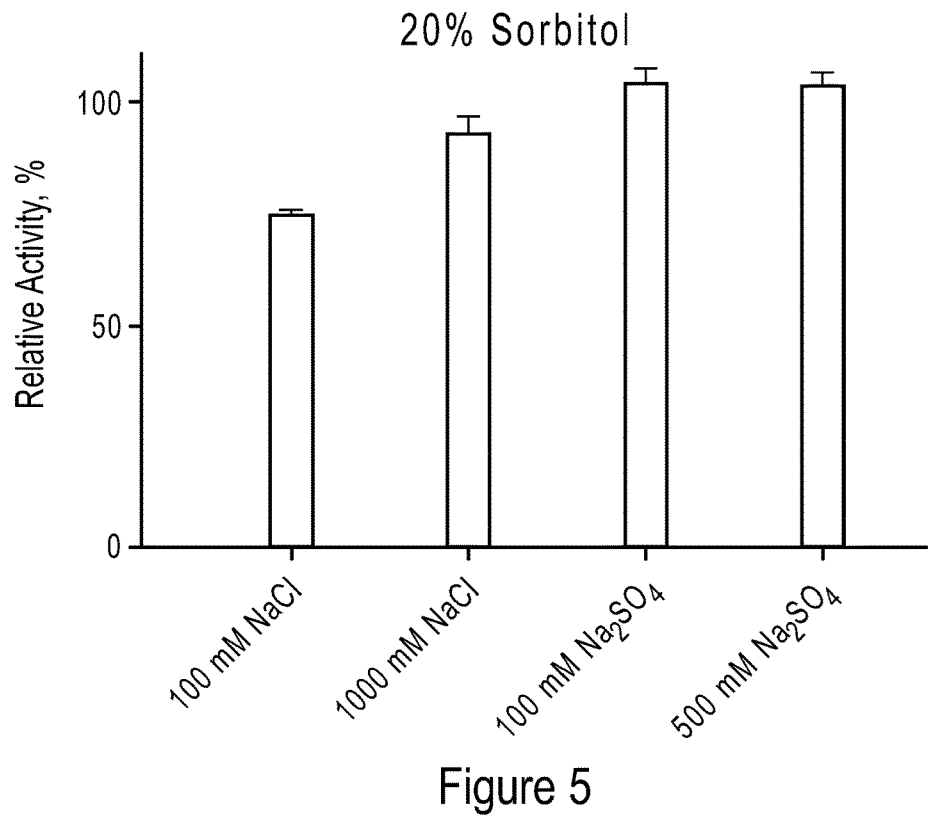
FIG. 5 shows NaCl- and $Na_2SO_4$-dependent effects on the stability of MMLV H– RT in the presence of 20% sorbitol. Enzyme was incubated for 5 days at +25° C. in the presence of different salts, and its activity was measured. 100 mM and 1000 mM of NaCl or 100 mM and 500 mM of $Na_2SO_4$ were added to the sorbitol buffer containing 50 mM Tris-Cl pH 7.5, 5 mM DTT, 1 mM EDTA, 0.1% Triton X-100, and 20% sorbitol.

FIG. 5 shows stabilization of target enzymes was observed in relation to increasing concentration of NaCl and Na$_2$SO$_4$. The catalytic activity of MMLV H– RT retained after 5 days at 25° C. was higher in buffers containing sorbitol when higher salt concentrations were used. Thus, higher salt concentrations significantly stabilize RTs in the presence of sorbitol, and higher salt concentrations and sorbitol may have synergistic effects.

Example 6: Analysis of Freeze-Thaw Stability

RT stability over cycles of freeze-thawing was tested. Enzyme was incubated for 20 cycles of 2 hours or more at −25° C. to 30 minutes at 22° C. and relative activity was measured compared to enzyme that did not undergo freeze-thawing. Enzymes were tested at 100 mM and 1000 mM of NaCl in buffer containing 50 mM Tris-Cl pH 7.5, 5 mM DTT, 1 mM EDTA, and 0.1% Triton X-100, and with or without 20% sorbitol.

Figure 6:
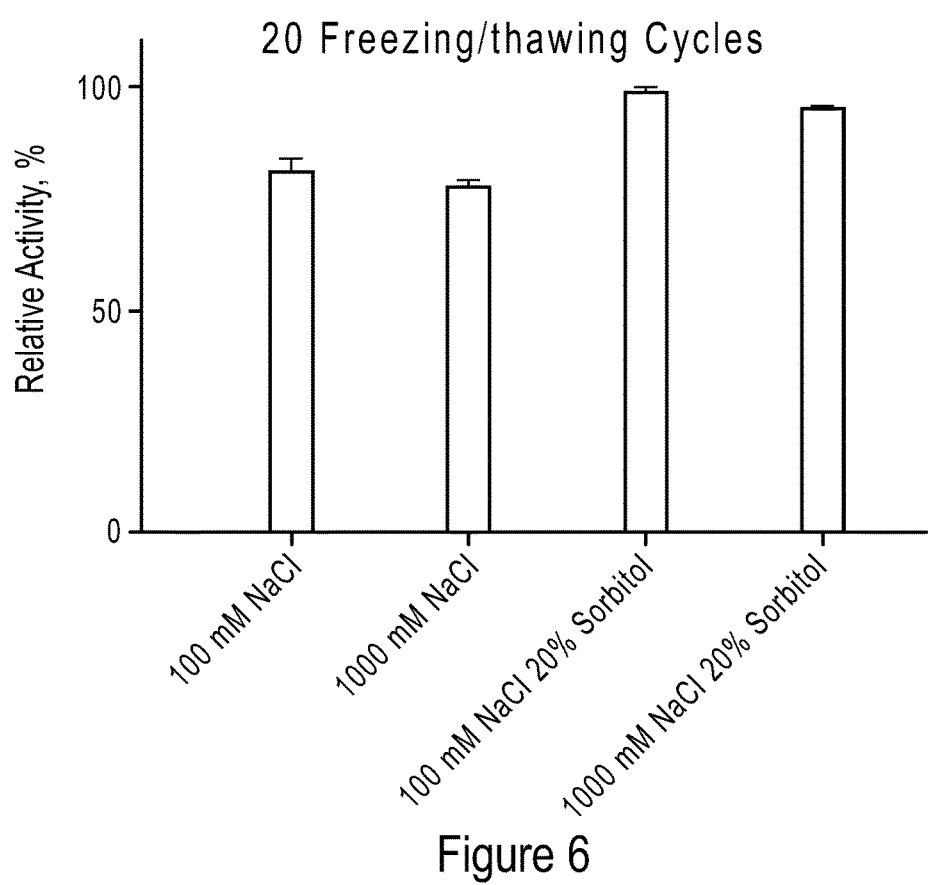
FIG. 6 shows effect of 20% sorbitol on the freeze-thaw stability of RT. Enzyme was incubated for 20 cycles of freezing-thawing (−25° C. and 22° C.), and its activity was measured. 100 mM and 1000 mM of NaCl was added to the buffer containing 50 mM Tris-Cl pH 7.5, 5 mM DTT, 1 mM EDTA, and 0.1% Triton X-100, and with or without 20% sorbitol.

FIG. 6 shows improved freeze-thaw stability was seen in formulations comprising sorbitol. High salt concentrations did not interfere with sorbitol's ability to stabilize the RT over freeze-thaw cycles.

Example 7: Comparison Analysis of Different Enzyme Conditions on Stability

In order to compare different enzyme buffer compositions, stability data was collected from experiments run on different days. For this experiment, RT relative activity was measured after 5 days at 25° C. in storage buffer (50 mM Tris pH 7.5, 1 mM EDTA, 5 mM DTT, 0.1% Triton X-100) plus the components listed in Table 3.

TABLE 3

Comparison analysis of relative activity of RT incubated in storage buffer comprising different components

| | | Formulation number | | | | | | | | |
|---|---|---|---|---|---|---|---|---|---|---|
| | | 1 | 2 | 3 | 4 | 5 | 6 | 7 | 8 | 9 |
| Inorganic salt | NaCl | 100 mM | 500 mM | 1000 mM | 1500 mM | | | | | |
| | KCl | | | | | 100 mM | 1000 mM | | | |
| | Na2SO4 | | | | | | | 100 mM | 500 mM | |
| | K2SO4 | | | | | | | | | 100 mM |
| | Glycerol | | | | | | | | | |
| | Sorbitol | | | | | | | | | |
| Activity after 5 days at +25° C. | | 20% | 73% | 77% | 85% | 25% | 76% | 82% | 99% | 72% |

| | | Formulation number | | | | | | | | |
|---|---|---|---|---|---|---|---|---|---|---|
| | | 10 | 11 | 12 | 13 | 14 | 15 | 16 | 17 | 18 |
| Inorganic salt | NaCl | | 100 mM | 1000 mM | | | 100 mM | 1000 mM | | |
| | KCl | | | | 100 mM | 500 mM | | | | |
| | Na2SO4 | | | | | | | | 100 mM | 500 mM |
| | K2SO4 | 500 mM | | | | | | | | |
| | Glycerol | | 50% | 50% | 50% | 50% | | | | |
| | Sorbitol | | | | | | 20% | 20% | 20% | 20% |
| Activity after 5 days at +25° C. | | 95% | 92% | 97% | 100% | 100% | 74% | 92% | 100% | 100% |

This analysis of results from different experiments shows that buffers lacking glycerol had a range relative activity after 5 days at 25° C. from 20% (with 100 mM NaCl, formulation 1) up to 99% (with 500 mM Na$_2$SO$_4$, formulation 8). These data highlight the dramatic effect of salt concentration on RT stability. Further, RT stability with high concentrations of sulfate salts were comparable to that seen with buffers comprising 50% glycerol (Formulations 11-14). In addition, solutions containing 20% sorbitol and high salt concentrations retained activity (Formulations 16 and 18). These data highlight that high salt concentrations stabilize RT enzymes and that sulfate salts may have particularly robust stabilizing effects.

Figure 7:
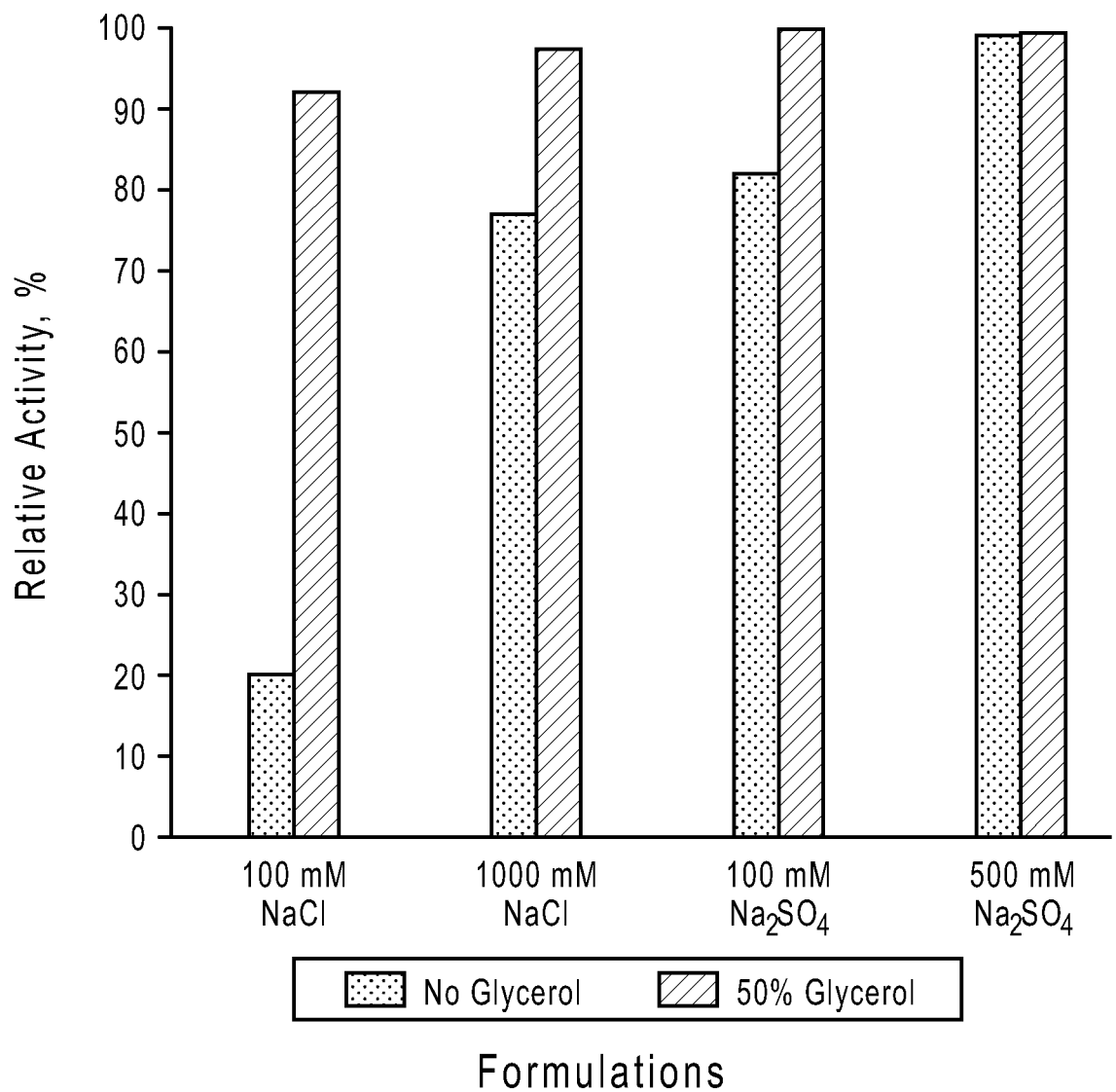
FIG. 7 shows comparison analysis of data from separate experiments on relative activity of different stabilized enzyme formulations with or without 50% glycerol.

FIG. 7 presents a comparison of different protein formulations comprising RT. Note that in some cases, comparisons are made between data from different experiments, and this comparison analysis is meant provide data on the effect of different formulations across different experiments. These data show high relative activity of RT in formulations with 1000 mM NaCl, 100 mM Na$_2$SO$_4$, and 500 mM Na$_2$SO$_4$ in the absence of glycerol. In particular, for formulations with Na$_2$SO$_4$, there was relatively less additional stabilization by glycerol.

This comparison analysis highlights the strong stabilizing effect of high salt concentrations, including sulfate salts. Some high salt formulations without glycerol attained stability equivalent to that seen with 50% glycerol formulations.

Example 8: Analysis of Lyophilization

One proposed advantage of glycerol-free RT solutions is the ability to successfully lyophilize the solution. Thus, the feasibility of lyophilization of glycerol-free RT solutions was assessed.

Glycerol-free reverse transcriptases (50 μl) were added to lyophilization vials and placed into a lyophilizer Telstar LyoBeta 25. Lyophilization was completed according to the following program: samples are frozen from 4° C. to −60° C. in 30 min and left frozen for 5 hours, then chamber vacuum was applied (0.135 mBar) and samples dried for 8 hours at −60° C., the temperature increased to −30° C. in 2 hours and incubated for 3 hours and then temperature was increased in steps from −30° C. up to 4° C. by keeping the duration of temperature increase for 1 hour and drying at each temperature for 3 hours. After lyophilization was completed, samples were dissolved in 50 μl of water and their relative activity was measured as described in the previous examples. Results are summarized in Table 4.

TABLE 4

Relative RT activity following lyophilization and reconstitution

| Enzyme | Activity, % |
|---|---|
| Maxima RT | 82.85 |
| Maxima H- RT | 78.62 |
| MMLV H- RT | 77.44 |
| Superscript III RT | 75.82 |

Thus, RT enzymes lyophilized from glycerol-free solutions retained activity. These values show a good retention of activity.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A stabilized enzyme formulation comprising:
   a. an enzyme and
   b. a glycerol-free buffer having high ionic strength comprising salt(s) providing Na+ and/or K+ ions,
   wherein the high ionic strength is at least 0.5 M ionic strength and further wherein the stabilized enzyme formulation retains at least 70% activity after storage for at least 5 days at 25° C. and/or at least 4 months at −20° C.,
   wherein the enzyme is a MMLV reverse transcriptase.

2. The stabilized enzyme formulation of claim 1, wherein the high ionic strength is from 0.5 M to 1.5 M ionic strength.

3. The stabilized enzyme formulation of claim 1, wherein the high ionic strength buffer comprises NaCl or KCl.

4. The stabilized enzyme formulation of claim 3, wherein the concentration of NaCl or KCl is from 500 mM to 1500 mM.

5. The stabilized enzyme formulation of claim 1, wherein the high ionic strength buffer comprises $Na_2SO_4$ or $K_2SO_4$.

6. The stabilized enzyme formulation of claim 5, wherein the concentration of $Na_2SO_4$ or $K_2SO_4$ is from 300 mM to 500 mM.

7. The stabilized enzyme formulation of claim 1, wherein the formulation further comprises at least one of:
   a) buffer salt(s);
   b) reducing agent(s);
   c) detergent(s);
   d) cryoprotectant(s); and/or
   e) optional other stabilizer(s).

8. The stabilized enzyme formulation of claim 1, wherein the reverse transcriptase is wildtype MMLV reverse transcriptase or a mutant MMLV reverse transcriptase.

9. The stabilized enzyme formulation of claim 1, wherein melting temperature of the enzyme increases as compared to the same enzyme in a buffer of 50 mM Hepes pH 7.0, 6.7 mM NaCl, 0.1 mM DTT, 0.27% sucrose, and 0.007 mM EDTA.

* * * * *

```
                        SEQUENCE LISTING

<160> NUMBER OF SEQ ID NOS: 4

<210> SEQ ID NO 1
<211> LENGTH: 683
<212> TYPE: PRT
<213> ORGANISM: Moloney murine leukemia virus

<400> SEQUENCE: 1

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335
```

```
Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Asn Ser Arg Leu Ile Asn
        675                 680

<210> SEQ ID NO 2
<211> LENGTH: 683
<212> TYPE: PRT
<213> ORGANISM: Moloney murine leukemia virus

<400> SEQUENCE: 2

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30
```

Trp Ala Glu Thr Gly Gly Met Gly Leu Ala Val Arg Gln Ala Pro Leu
         35                  40                  45

Ile Ile Pro Leu Lys Ala Thr Ser Thr Pro Val Ser Ile Lys Gln Tyr
 50                  55                  60

Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
                115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
                210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Glu Ala Arg Lys Glu Thr Val
                275                 280                 285

Met Gly Gln Pro Thr Pro Lys Thr Pro Arg Gln Leu Arg Glu Phe Leu
                290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
                435                 440                 445

-continued

```
Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Ala Gly Ser Ser Leu
            515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
    595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Asn Ser Arg Leu Ile Asn
            675                 680

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: misc_feature
<222> LOCATION: (1)..(20)
<223> OTHER INFORMATION: /note="This sequence may encompass 18-20
      nucleotides"

<400> SEQUENCE: 3
tttttttttt tttttttttt                                              20

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tttttttttt tttttttt                                                18
```